(12) United States Patent
Mifsud et al.

(10) Patent No.: US 6,290,838 B1
(45) Date of Patent: Sep. 18, 2001

(54) APPARATUS AND METHOD FOR CHARACTERIZING LIQUIDS

(75) Inventors: Jean-Christophe Mifsud; Quitterie Lucas, both of Toulouse (FR)

(73) Assignee: Alpha M.O.S., Toulouse (FR)

( * ) Notice: Subject to any disclaimer, the term of this patent is extended or adjusted under 35 U.S.C. 154(b) by 0 days.

(21) Appl. No.: 09/380,663

(22) PCT Filed: Mar. 6, 1998

(86) PCT No.: PCT/FR98/00449

§ 371 Date: Nov. 22, 1999

§ 102(e) Date: Nov. 22, 1999

(87) PCT Pub. No.: WO98/39648

PCT Pub. Date: Sep. 11, 1998

(30) Foreign Application Priority Data

Mar. 6, 1997 (FR) .................................................. 97 02668

(51) Int. Cl.$^7$ ...................................................... G01F 1/64
(52) U.S. Cl. ...................... 205/775; 205/777.5; 205/789; 205/793.5; 204/400; 204/403; 204/412; 204/416; 204/418; 422/61; 422/68.1
(58) Field of Search ...................................... 204/400, 403, 204/412, 416, 418; 205/775, 789, 793.5, 777.5; 422/52, 55, 58, 61, 68.1, 82.01, 82.03, 82.05, 82.12

(56) References Cited

U.S. PATENT DOCUMENTS

| 4,109,527 | * | 8/1978 | Goode, Jr. | ............................ 374/142 |
| 5,373,452 | | 12/1994 | Guha | ..................................... 364/550 |

FOREIGN PATENT DOCUMENTS

| 0 410 356 | | 1/1991 | (EP) . |
| 464 820 | | 1/1992 | (EP) . |
| 763 729 | | 3/1997 | (EP) . |
| 2033583 A | * | 5/1980 | (GB) . |
| 95 08113 | | 3/1995 | (WO) . |
| 39 32420 | | 11/1995 | (WO) . |

OTHER PUBLICATIONS

CAPLUS abstract of Weimar et al. ("Hybrid sensor arrays for gs and odor analysis", Book of abstracts, 212th ACS National Meeting, Orlando, FL, Aug. 25–29 (1996)).*

A. Legin, et al. "Tasting of Beverages Using an Electronic Tongue Based on Potentiometric Sensor Array", Sep. 1996, Eurosensors X, pp. 427–430.

K. Toko, "Electronic Sensing of the Taste of Beer and Other Foodstuffs", Dec. 1995, International Electron Devices Meeting (IEDM), pp. 143–148.

T. Fukunaga, et al., "Quantification of Taste of Coffee Using Sensor with Global Selectivity", 1996, Sensors and Materials, vol. 8, No. 1, pp. 47–56.

* cited by examiner

Primary Examiner—T. Tung
Assistant Examiner—Alex Noguerola
(74) Attorney, Agent, or Firm—Weingarten, Schurgin, Gagnebin & Hayes LLP

(57) ABSTRACT

An apparatus and a method of characterising liquids employ liquid sensors of different types of technology, in order to generate characterisation data from the whole of the output signals originating from these sensors when they are soaked in a sample of the liquid. The set of sensors may comprise: lipid sensors, quartz microbalances, ion-selective electrodes, biosensors, chemical microelectrodes or even, in certain particular applications, fiber optic based-sensors. The output signals originating from the different sensors are normalized with respect to values which are determined in a prior standardization operation during which the sensors were soaked in at least one sample reference liquid.

18 Claims, 5 Drawing Sheets

APPARATUS AND METHOD FOR CHARACTERIZING LIQUIDS

The present invention relates to methods and to apparatuses which are intended for characterising liquids, i.e. methods and apparatuses which are capable of generating data which characterise a sample of liquid which is provided to them. The invention especially relates to methods and to apparatuses which aim to distinguish liquid products from one another and/or to identify liquids. The invention enables, inter alia, an ultra-rapid quality control of liquid matrices.

It is often necessary to characterise samples of liquid, for example for the quality control of liquid matrices such as water, milk, wine, etc., and in fields as varied as agri-foodstuffs, cosmetics, the environment and the medical field. The classical techniques used to this end are liquid chromatography, GC/MS (gas chromatography+mass spectrometry) or capillary electrophoresis or analysis carried out which uses ion-selective electrodes. Such methods characterise the samples whilst at the same time determine the chemical composition of these or, at least, the content, in the sample, of a particular compound.

Such methods are long and costly to implement. The average analysis time in liquid chromatography, for example, is situated between 10 and 20 minutes. Furthermore, most of the time, a preparation of the sample is necessary.

In the aim of reducing the time necessary for characterising liquids, certain researchers have proposed adopting an approach based not upon the identification of the components making a part of the liquid, but upon an overall characterisation of the liquid. This approach consists of using sensors which are sensitive to multiple components at the same time, which generate representative signals from the liquid, and in the use of techniques of recognition of units in order to create, from these signals, <<an impression>> of the liquid (i.e. data characterising the liquid). For example, in the article: <<Tasting of beverages using an electronic tongue based on potentiometric sensor array>> by Legin et al (Eurosensors X, Leuven, Belgium, $8^{th}$–$11^{th}$ September 1996), an apparatus is described which is intended for a use in the quality control of drinks, this apparatus comprising a group of chemical sensors in the solid state. The characterisation of foods is treated in the book <<Characterisation of Food: emerging methods>> (ed. A. G. Gaonkar, Elsevier Science, 1995), in the sixteenth chapter of which liquid sensors are proposed the voltage change of which varies in the presence of liquids having different gustative characteristics.

However, up to the present day, no apparatus of detection by impression in liquid matrices has resulted from the various theoretical propositions. One of the reasons which would explain this lack consists in this fact that in practice, any apparatus for characterising liquids must have a high discrimination capacity from which a high enough capacity to differentiate various liquids. It has been discovered that the sensors must be non-specific or not very specific, the detection of a given compound originates therefore from crossed factors of sensors. In the devices which have been proposed up to now, the sensors are too selective and specific to enable the rapid detection of a given compound.

The aim of the present invention is a method and an apparatus for characterising liquids having a high resolution and which are capable of arriving rapidly at a reliable characterisation of a sample of liquid, and this by the development of non-selective sensors, of large specificity, and the crossing of sensors of different types of technologies. In the case in which from the group of sensors employed there exists a plurality of sensors of a same type of technology, it can prove to be advantageous to manufacture the latter in using various depositing means so as to obtain various thicknesses of coating or of sensitive element and, therefore, sensors the specificity of which varies.

More particularly, the present invention provides a method and an apparatus according to which at least one measuring electrode intended to be soaked in a sample of liquid to be characterised is (are) equipped with sensors of at least two different types of technology, i.e., sensors which have respective physical or chemical reactions of different nature during the immersion of the sensor concerned in a liquid. The output signals from these sensors used in the apparatus according to the invention are captured and processed in order to determine an impression for the liquid concerned.

One of the main advantages of the present invention consists of its high capacities of resolution and of discrimination obtained by virtue of the use of signals originating from liquid sensors of several types of technology.

Preferably, the sensors of different types of technology are selected from the group consisting of lipid sensors, quartz microbalances, surface acoustic wave device sensors, also known under the name of SAW devices, ion-selective sensors, biosensors, and chemical microsensors. The sensors of the technologies of this group are non-selective or not very selective, i.e. that instead of reacting with one sole component of the sample or with one sole main gustative principle (sweet, salty, etc.), they react in an overall manner with the <<taste>> of the liquid. In other terms, each sensor reacts with several of the main gustative qualities. (This group could be enlarged in case of development of sensors according to a new type of technology). When these sensors are soaked in a liquid, their electrical or piezoelectrical properties change, for example, the voltage, the electrical resistance, the frequency of oscillation, etc.

The samples of liquids interact with the sensors of different types of technology according to the chemical or physical processes of different nature. The output signals from the respective sensors of different technologies therefore reflect the different properties of the samples of liquids and/or of the components of these. The use of several technologies leads, during the analysis of various liquids, to an increase in the variability of the signals and therefore increases the capacity of discrimination of the apparatus.

In certain applications, it could prove to be useful to associate sensors of different types of technology with sensors of one sole type of technology comprising layers deposited according to different procedures. Preferably, in these sensors of the same type of technology, the thickness or the composition of at least one respective sensitive layer of these sensors varies. This enables increasing the capacity of discrimination of the system even further.

It can also prove to be interesting to associate, with the signals originating from the main sensors, additional data of classical chemical analysis such as the pH, the oxygen content, the $CO_2$ content, the chlorine content, the measurement of a specific compound or finally the colour.

The method and the apparatus according to the present invention give, in a few seconds, a result which is equivalent to that given after 10 to 20 minutes by a chromatography system. Further, according to the present invention, no preparation of the sample is necessary.

The instruments according to the preferred embodiments of the invention enable having an impression which characterises a sample of liquid and enable comparing it to a learning base or database so as to detect or to identify the liquid concerned. This learning base or database is established during a learning phase of the system. Once the learning phase of the system is accomplished, the system can be used by a person who has no training in the field of analysis.

The instruments according to the preferred embodiments of the invention enable an ultra-rapid characterisation of liquids. They offer a very wide variety of applications in fields such as the quality control of liquid matrices, as well as in many other fields a few examples of which are set forth at the end of the description. These instruments enable quantitative and qualitative measurements in associating non-specific liquid sensors of several types of technology or of depositing procedure, and preferentially of artificial intelligence of the neural network type or fuzzy logic type, or even of methods known as <<chemometric>> methods which enable the recognition of the impressions of each sample and, therefore, of each quality.

These instruments further enable making very rapid correlations between measurements made by the apparatus and tastes detected by sensory panels—an indication of the evaluation of the tastes by the sensory panel being furnished to the instrument during the learning phase.

In a preferred embodiment of the invention, there is a prior standardisation phase of the system. This consists in the capturing of the values of the output signals originating from the various sensors when they are soaked in one or more reference samples. These products are used for enclosing the products to be analysed so as to follow and correct the drift of the sensors with time.

The reference samples are advantageously constituted of products which compose the matrix which will be analysed afterwards. For example, in the case of an analysis made on a wine, the reference products can consist of succinic acid, citramalic acid, and galacturonic acid. In the case of food analysis, the reference samples can correspond to particular gustative qualities such as bitter, sweet, salty, sour, or to other chemical or qualitative qualities. In other applications, it is suitable to use salts or even natural products which constitute the product to be analysed, as a reference sample.

The intensity of the output signals originating from the sensors depends upon the concentration of the liquid which is the subject of the analysis. Effects due to a variation in the concentration of the liquid can be compensated, if desired, by normalising the output signals obtained for each one of the samples.

Furthermore, after the measurements, notably of fatty matrices such as butters and oils, the surfaces of the sensors become less reactive. It is thus preferable to regenerate the sensors between each measurement, or every <<x>> measurements, by soaking the measuring electrodes, and optionally the reference electrode, in samples of appropriate cleaning liquids.

Particular embodiments of the present invention will now be described as non-limiting Examples, in connection with the annexed Drawings in which:

FIGS. 1A and 1B are schemes which illustrate the constitution of an automatic measuring apparatus according to a preferred embodiment of the present invention, in which:

FIG. 1B is a scheme illustrating the apparatus.

FIGS. 4A and 4B are graphs which illustrate the increased capacity of the apparatus according to the invention for distinguishing between samples of milk at various stages of degradation, in which:

FIGS. 6A and 6B are graphs which illustrate the increased capacity of the apparatus according to the present invention to distinguish between samples of liquid wastes of various types, in which:

The method and the apparatus provided by the present invention will now be described as a whole with the aid of FIG. 1 which shows an embodiment of an automatic apparatus for characterising liquids according to the invention. Several operations carried out by the automatic apparatus could be made manually. However, the automatic functioning enables ensuring a better repeatability of the measuring conditions and better capacities of discrimination and resolution for the system result therefrom.

Figure 1A:
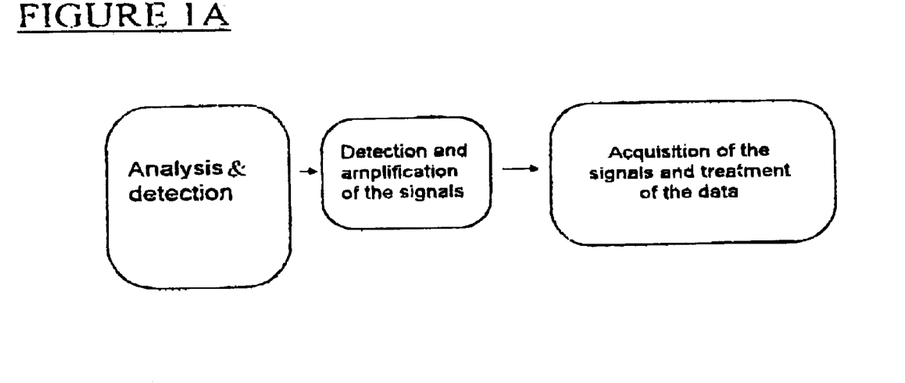
FIG. 1A is a functional scheme.

As can be seen in the functional scheme of FIG. 1A, the automatic apparatus according to this embodiment is constituted of three main parts, a first part of detection or of analysis of a sample of liquid, a second part of detection and of amplification of the signals originating from the first part of the system, and a third part of processing of the signals acquired by the second part.

Figure 1B:
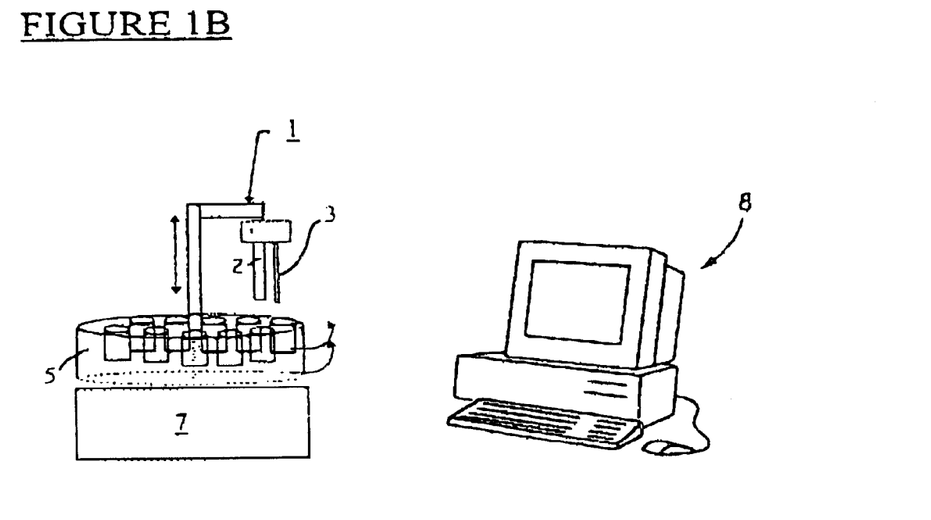

In FIG. 1B, it is seen how these three parts of the system can be presented in practice. More particularly, the first part of the system comprises a measuring head 1 equipped with (at least) one measuring electrode 2 and optionally with a reference electrode 3. Liquid sensors 10 of several different types of technology are disposed on the measuring electrode 2. Various samples of liquids are loaded into the carousel 5, equipped with a heating system, and intended to turn so as to position each sample in turn next to the measuring head 1. The measuring head 1 is disposed at the end of a motorised arm by means of which the head is displaced so as to insert into, and to remove from, the sample of liquid, the measuring electrodes and reference electrodes, 2 and 3. The second part of the system comprises electronic circuits 7 of detection and of amplification of the signals originating from sensors 10, or known types. The third part of the system is constituted, normally, by a computer or data processing system 8 the functioning mode of which is commanded by suitable software. This data processing system 8 carries out the processing of the signals emanating from sensors 10 so as to generate data which characterise the sample to be tested.

Figure 2:
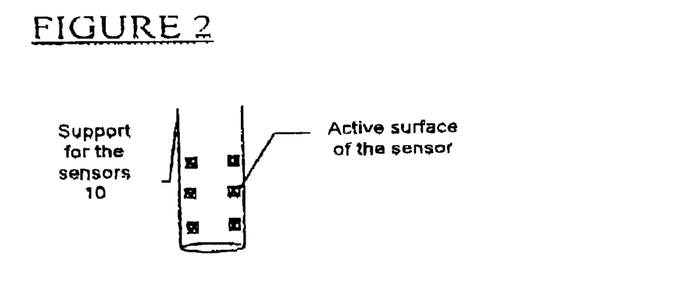
FIG. 2 is a scheme which illustrates the arrangement of the sensors on a measuring electrode according to the preferred embodiment of the present invention.

Before considering the preferred characteristics of the system as a whole, the measuring head 1 will first of all be described in greater detail in referring to FIG. 2.

As can be seen in FIG. 2, the measuring head 1 consists of a full cylinder on which detectors or sensors 10 disposed on a support, and a reference electrode 3, are fitted. The whole of the sensors 10 and their support constitutes the measuring electrode 2. The reference electrode can be separate from or integral with the sensors support 10.

It is not compulsory that the sensors be found all on a same support, it being possible for these to be disposed on different supports. Similarly, the reference electrode is necessary in the case of use of lipid sensors or electrochemical-type sensors, but can be omitted in other cases. The reference electrode can be integral or not with the support or one of the supports bearing the sensors.

According to the present invention, the system is equipped with sensors of several types of different technologies. The different technologies which are the most interesting in this regard comprise: sensors known as <<lipid sensors>>, quartz microbalances, surface acoustic wave device sensors, also known under the name of SAW devices, ion-selective electrodes, chemical microelectrodes, biosensors and, in certain very particular applications, fibre optic-based sensors.

Surface acoustic wave device sensors may be preferable to quartz microbalance sensors due to their better sensitivity.

In the case of use of lipid sensors, the signal measured consists of the difference in voltage which exists between these sensors and the voltage of the reference electrode 3 (this latter being typically a silver electrode). Lipid sensors are manufactured typically according to a method such as the following:

the lipids (for example, dioctyl phosphate, cholesterol, oleic acid, decyclic alcohol, trioctylmethylammonium chloride, etc.) are mixed in a tube with poly(vinyl chloride) (PVC) and a plasticiser (for example dioctyl phenyl phosphate) all three dissolved in tetrahydrofuran. This mixture is then coated on a glass plate and is dried at 30° C. by a controlled drying operation. The sensitive element thus prepared has a desired thickness (for example, 200 $\mu$m) and is connected to a silver electrode.

Quartz piezoelectrical devices which are commonly used in the field of mobile telephones can be made use of as quartz microbalances. In fact, it is appropriate to recall that, once soaked in a liquid, the frequency of oscillation of these devices changes according to the liquid. These quartz microbalances (QMB) are manufactured in general by depositing a liquid chromatography coating. These coatings are typically of the C18 type.

One or more surface acoustic wave device sensor(s) (SAW devices) can also be used, the technology of which is well-known in the field envisaged, and will therefore not be described here due to conciseness concerns.

The ion-selective electrodes are well known in the field of classical chemical analysis and they will not therefore be described here. It is sufficient to remark upon the fact that they comprise, inter alia, ISFETs and MEMFETs.

As regards the chemical microelectrodes, biosensors and fibre optic-based sensors, known devices can be employed.

It is preferable to use several sensors of each one of the technologies selected. The sensors used of a same technology can be identical or different, according to the application. The selection of the sensors is made, notably, as a function of the molecules which are present in the liquid matrices to be studied and which will be analysed afterwards. However, advantageously, the selection is made also from a function of the software which enables calculating the discriminating power of the sensors. More particularly, the discriminating power of each one of a group of sensors can be calculated during an analysis carried out on a sample which is similar to the matrix which will be studied afterwards. The sensors having the highest discriminating power will be retained.

Figure 3:
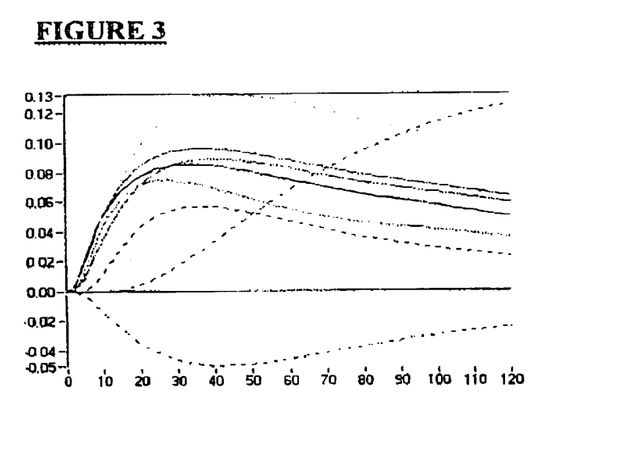
FIG. 3 is a scheme which indicates the output signals originating from a group of sensors in the case of an analysis of a sample of wine.

When the measuring electrode 2 is soaked in a sample of liquid, the electrical and piezoelectrical properties of the different sensors will change and, one corresponding change of the output signal originating from each sensor is produced. Normally, this change evolves with time. For example, FIG. 3 shows the evolution with time of the output signals originating from 8 sensors (4 lipid sensors and 4 quartz microbalance sensors or surface acoustic wave device sensors) which have been soaked in a sample of wine.

An impression characterising the sample of liquid can be determined from the whole of the output signals originating from the sensors. According to the applications, the impression will be based on the different characteristics of the output signals, such as:

the value of the output signal at a specific moment after the start of the measuring operation (i.e. after the insertion of the measuring electrode in the sample of liquid), the maximum value of the output signal during a measuring interval of a particular duration, the relation between this measuring interval and the moment of insertion of the measuring electrode in the sample of liquid being fixed, the manner in which the output signal evolves during the measuring period.

The best impression for characterising a particular liquid can comprise information concerning various characteristics of the output signals from the various sensors. It is preferable to fix the choice of sensors and of interesting characteristics of the output signals as a function of the application sought after, by carrying out a preliminary experimentation phase which uses samples of known nature or quality.

The apparatus of FIG. 1 will now be considered in greater detail in starting with the <<sampling>> part.

The samples are placed in recipients which are placed on the carousel 5. No preparation of the samples being necessary, the samples (orange juice, cognac, water, etc.) can be poured as such directly into the recipients or, if desired, a filtering step or similar step can be accomplished beforehand for viscous liquids or semi-viscous liquids such as orange juice with pulp, tomato juices or decantation basin waters. In this Example, carousel 5 comprises places for 8 to 20 recipients. It can prove to be useful to equip the carousel 5 (or other sample container) with a device for controlled heating and/or with means of agitation—in certain applications, a better reproducibility of the measurements is obtained when the output signals originating from the sensors 10 are captured while the product is maintained at a certain temperature and/or after agitation of the sample. Carousel 5 (or other samples container) can be equipped with a cover so as to protect the fragile samples, the cover being removed just before each analysis.

According to a particularly preferred embodiment of the present invention, reference samples are loaded onto the carousel 5. These reference samples correspond to products which are associated with the liquid which will be analysed afterwards and enable a standardisation of the system so as to remove the effects due to the drift of the sensors.

More specifically, the measuring electrode(s), and optionally the reference electrode, are soaked in each one of the reference samples and the output signals from the sensors are captured. The values captured during this standardisation step are processed and compared with the values determined beforehand during an analysis made on samples of the same nature as the reference samples. This comparison enables determining the transformation or the calculation necessary so as to coincide the processed data originating from the standardisation step and the data determined beforehand. Afterwards, during the measuring step, this same transformation will be used either for normalising the data resulting from the processing of the output signals from the sensors, or for normalising the learning base/database established during the learning phase of the system.

As has already been specified above, the nature of the reference samples depends upon the nature of the matrix to be characterised. In the case of characterisation of foods, it is often convenient to use, as reference samples, products which correspond to main gustative principles. For example, for sugar, a sample of sucrose, or preferably a $10^{-4}$ M glucose solution, can be used, for sour, a 0.1 M or $10^{-4}$ M hydrochloric acid sample, for salty, a $10^{-2}$ M sodium chloride (NaCl) solution, and for bitter, a 0.1 M quinine solution or preferably a $10^{-3}$ M aspirin solution can be used or, for applications for coffees or carbonated drinks, a $10^{-3}$ M caffeine solution can be used. Other compounds can also be used as a function of the application envisaged: notably aspartame in the case of application concerning low calorie content drinks (<<light>> drinks), succinic acid, citramalic acid or galacturonic acid in the case of analysis of wine and, in other cases, salts or natural products constituting the product to be analysed.

It is preferable, also, to lead the carousel 5 with other samples, such as solutions of ethanol or butanol at 5%, which enable a rapid regeneration of the surfaces of the sensors in the case of a partial poisoning, notably in the case of fatty matrices (butters, oils, . . . ), and which enable therefore rinsing the measuring head. The rinsing or cleaning of the surfaces of the sensors consists, preferably, of soaking the sensors in water for a period of 2 to 5 minutes. Other liquids which can be used advantageously for this soaking are an 80% ethanol solution with 20% water; or a 20% butanol solution with 80% water; or a 20% ethanol solution with 80% water.

As has been specified above, the data processing system carries out a processing of the output signals which originate from the sensors so as to characterise, to detect or to recognise the liquid to be tested. This processing comprises establishing a database and/or a learning base, as well as a classification of the sample undergoing analysis carried out using the database and/or the learning base. Known statistical methods of multidimensional analysis can be applied, as well as methods known as <<chemometric>> methods. An artificial intelligence of the <<neural network>> type is particularly useful when it is a matter of recognising liquids.

The statistical and chemometric methods as well as the methods of processing based on neurone networks are well known—see, for example, the following references: G. Saporta <<Probabilités, Analyse de données et Statistiques>> (Editions Technip, 1990, Paris, pp. 165–179); J. Herault et al. <<Réseaux Neuronaux et traitement du Signal>> (Traité des nouvelles technologies, série traitement du signal, Editions HERMES, 1995, Paris); A. Hierlemann et al. <<Sensors update>>, Volume 2 (Editions H. Baltes, W. G öpel, J. Hesse, Edition VCH, 1996, pp. 121–155 <<Pattern recognition and multicomponent analysis>>). Consequently, these methods and processes will not be described here in greater detail.

In this embodiment, the data processing system 8 controls the progress of each measuring operation of the system and, optionally, controls the implementation of the standardisation and/or learning phases. Thus, by means of the robotised arm, the data processing system 8 controls the agitation of the flasks (for example, by magnetic stirring) and their stabilisation, as well as the rinsing of the measuring head. The data processing system 8 controls, also, the detection time, the acquisition of the signals, the processing of the linear (statistical) data or non-linear (neural network) data, and the visualisation of the signals (for example on a monitor) in the form of curves, graphs or any other suitable form.

Results of analyses carried out by using an example of an apparatus according to the invention will now be described.

EXAMPLE 1

Figure 4A:
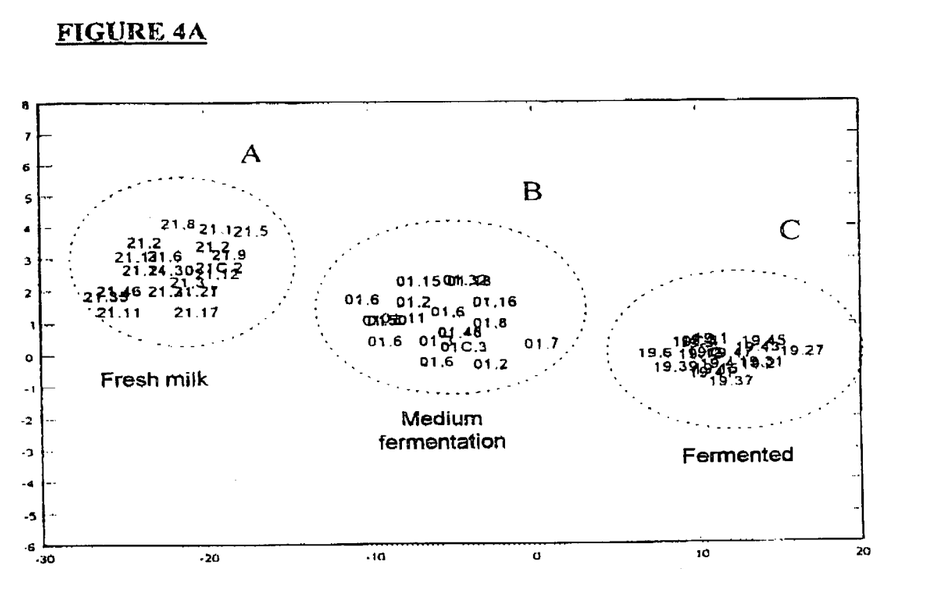
FIG. 4A is a graph prepared according to an analysis of main components and which illustrates the results obtained in employing a measuring electrode according to an embodiment of the invention.
Figure 4B:
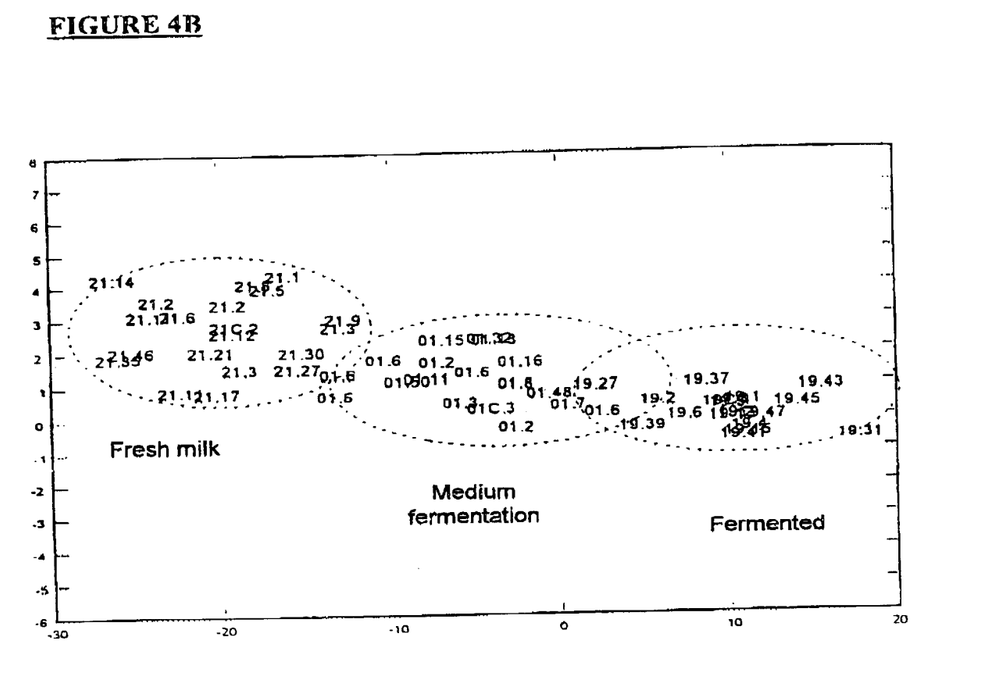
FIG. 4B illustrates comparative results obtained in employing a measuring electrode bearing sensors of one sole type of technology.

Detection of the Degradation of Milk (FIGS. 4A and 4B)

FIGS. 4A and 4B are graphs which each represent the results of an analysis of main components which was carries out on a respective set of output signals originating from the sensors present on a respective measuring electrode soaked successively in several different samples of milk. FIG. 4A relates to the results obtained in using a measuring electrode according to the present invention. FIG. 4B relates to the results obtained by employing a measuring electrode bearing sensors of one sole type of technology.

The samples of milk were of three different qualities: fresh milk, fermented milk and milk undergoing fermentation. This experiment is used in the learning of the system in the recognition of samples of milk of different qualities. In this Example, 18 samples were used of each quality of milk so as to measure the variability within each group. However, the number of samples employed during the learning must be at the minimum equal to the number of sensors used.

In this experiment, the measuring electrode according to the invention comprised 4 lipid sensors and 4 ISFET sensors the characteristics of which were the following:

Lipid sensor 1: sensitive layer of thickness 150 μm, of dioctyl phosphate, deposited by atomisation.

Lipid sensor 2: sensitive layer of thickness 300 μm, of oleic acid, deposited by atomisation.

Lipid sensor 3: sensitive layer of thickness 200 μm, of decyclic alcohol, deposited by atomisation.

Lipid sensor 4: sensitive layer of thickness 400 μm, of triocrylmethylammonium, deposited by atomisation.

ISFET sensor 1: $20AgI$-$40Ag_2S$-$40GeS_2$, membrane prepared according to the photolithographic technique.

ISFET sensor 2: $PbI_2$-$Ag_2S$-$As_2S_3$, membrane prepared according to the photolithographic technique.

ISFET sensor 3: $AgCl$-$Ag_2S$, membrane prepared according to the photolithographic technique.

ISFET sensor 4: $Sb_{metal}$, membrane prepared according to the photolithographic technique.

This measuring electrode and a silver reference electrode were soaked in each sample of milk for a period of 15 seconds. The output signals of each sensor, and of the reference electrode, were captured as from the insertion of the electrodes in each sample of milk and they were measured every second over a period of 120 seconds. The output signals originating from the lipid sensors were normalised by deduction of the voltage of the output signal from the reference electrode. The maximum values of the output signals from the sensors during the capture interval were determined and were then made the subject of an analysis of main components. According to this analysis, the information brought by the whole of the sensors is placed on two axes, as can be seen from the graph of FIG. 4A. This calculation employs one of the methods of multivaried statistical analysis known as <<chemometric>>.

As a Comparative Example, the experiment described above was repeated in using a measuring electrode bearing only five QMB sensors the coatings of which were similar to those of the QMB sensors used in Example 3 described below. The results of this experiment are illustrated in FIG. 4B.

From the graph of FIG. 4A, it is seen clearly that the system according to the invention has been able to differentiate the different samples of milk as a function of their quality, grouping the samples into three different groups or territories A, B and C, according to their quality. Moreover, it emerges clearly from a comparison of FIGS. 4A and 4B that the apparatus according to the present invention enables differentiating samples of different nature, whereas an apparatus equipped with an electrode bearing sensors of one sole type of technology is less able to clearly distinguish the different classes, and this proves the interest in using different technologies.

If the system according to the invention is intended not only for classifying samples into groups, but also for identifying the groups, then the territories formed by the statistical analysis must be correlated with external data such as other chemical data or evaluations originating from a sensory panel. The classes recognised by the system as well as the external data associated with these during the learning phase are used to establish a model for use during the analysis phase.

During the analysis phase, unknown samples are analysed and the output signals obtained are injected into the system. These samples are then classified into one of the classes defined above. In this example concerning milk, each territory was correlated to a quality of milk. Each unknown sample is replaced in one of these territories and its quality is therefore known.

EXAMPLE 2

Figure 5:
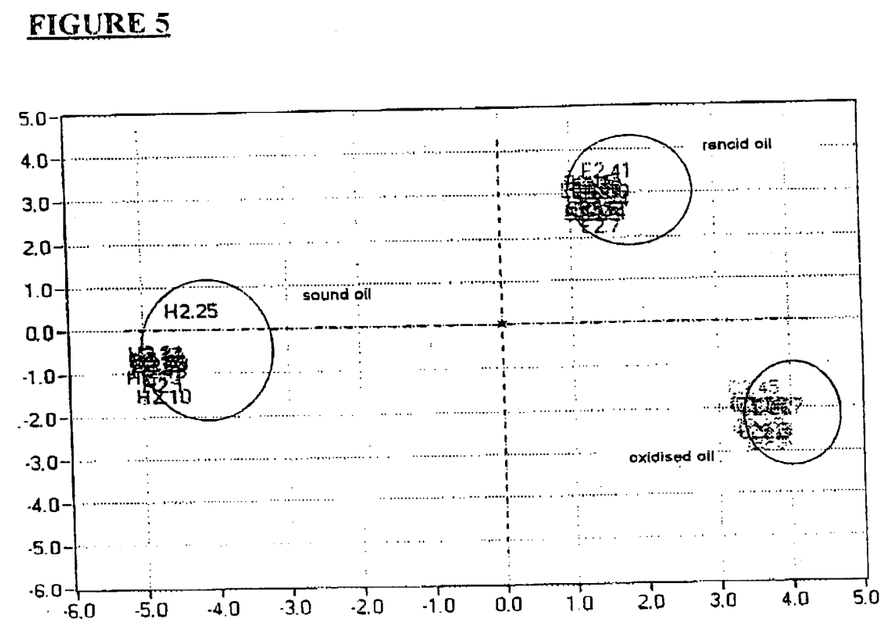
FIG. 5 is a graph, prepared according to an analysis of main components, which illustrates the capacity of the apparatus according to the present invention to distinguish between samples of oil at various stages of degradation.

Detection of the Degradation of Oil (FIG. 5)

The graph of FIG. 5 illustrates a quality control made on samples of oil and carried out in a similar manner to the experiment described above.

In the present experiment, several samples of oil were tested, notably samples of sound oil, rancid oil and oxidised oil. Once again, if this experiment corresponds to the learning phase of the system aiming to establish a model, the number of samples used is not important, from the moment at which the number of the sample per class be equilibrated, that the number of analyses be greater than the number of samples, and that the samples be representative of the matrix which will be analysed afterwards.

The measuring electrode used in this experiment bore 6 lipid sensors and 4 quartz microbalances the characteristics of which were the following:

Lipid sensor 1: sensitive layer of thickness 200 $\mu$m, of dioctyl phosphate, deposited by syringe.

Lipid sensor 2: sensitive layer of thickness 150 $\mu$m, of oleic acid, deposited by atomisation.

Lipid sensor 3 sensitive layer of thickness 200 $\mu$m, of decyclic alcohol, deposited by atomisation.

Lipid sensor 4 sensitive layer of thickness 300 $\mu$m, of trioctylmethylammonium, deposited by atomisation.

Lipid sensor 5 sensitive layer of thickness 100 $\mu$m, of cholesterol, deposited by atomisation.

Lipid sensor 6 sensitive layer of thickness 400 $\mu$m, of cholesterol, deposited by syringe.

QMB sensor 1: sensitive layer of thickness 300 $\mu$m, of octadecyl and cyano phase on silica 5 $\mu$m, deposited by soaking.

QMB sensor 2: sensitive layer of thickness 150 $\mu$m, of polystyrene sulphonate phase based on a resin, deposited by soaking.

QMB sensor 3: sensitive layer of thickness 200 $\mu$m, of phenyl phase linked to a polymer in the form of a gel, deposited by soaking.

QMB sensor 4: sensitive layer of thickness 250 $\mu$m, of diamine phase on silica phase 5 $\mu$m, deposited by soaking.

The measuring electrode and a silver reference electrode were soaked in each sample of oil for a period of 60 seconds. The output signals from each sensor, and from the reference electrode, were captured as from the insertion of the electrodes in each sample of oil and they were measured every second over a period of 120 seconds. The output signals originating from the lipid sensors were normalised by subtraction of the voltage of the output signal of the reference electrode. The maximum values of the output signals from the sensors during the capture interval were determined and were then made the subject of an analysis of the main components as in the preceding Example. The results of this analysis are given in FIG. 5.

From the graph of FIG. 5, it is seen clearly that the system has been able to differentiate between the different samples of oil as a function of their quality.

It will be noted that it would also have been possible for the measurements made in this Example to be made by using surface acoustic wave device sensors instead of the QMB sensors, as well as by using a combination of surface acoustic wave device sensor(s) and QMB sensor(s).

EXAMPLE 3

Figure 6A:
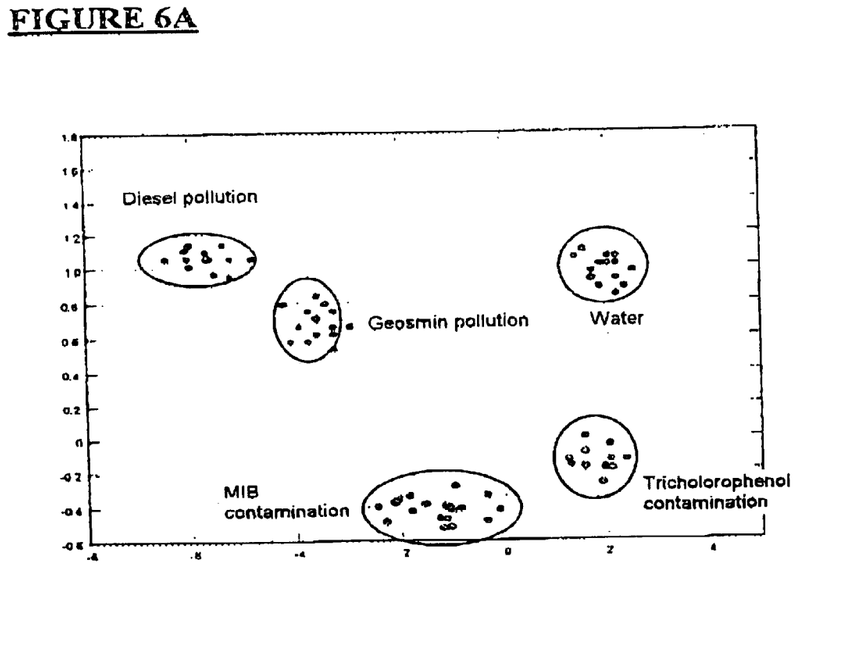
FIG. 6A is a graph prepared according to an analysis of main components and which illustrate results obtained in employing a measuring electrode according to an embodiment of the invention.
Figure 6B:
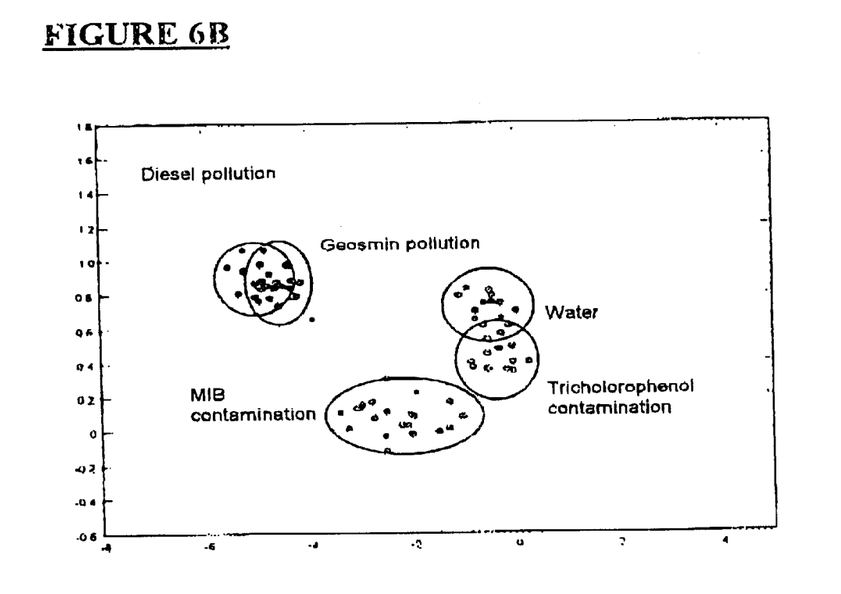
FIG. 6B illustrates comparative results obtained in employing a measuring electrode bearing sensors of one sole type of technology.

Differentiation Between Different Types of Pollution (FIGS. 6A and 6B)

The graphs of FIGS. 6A and 6B illustrate a quality control made on samples of water, mostly polluted, and was carried out in a similar manner to the first example described above.

In the present experiment, several samples of water were tested, notably of samples of non-polluted water, water polluted by diesel, water polluted with geosmin, water polluted with trichlorophenols, and water polluted with methyl isoborneol (MIB).

The measuring electrode according to the invention used in this experiment bore 5 quartz microbalance sensors and 3 ISFET sensors. There was no reference electrode. The characteristics of the sensors were the following:

QMB sensor 1: sensitive layer of thickness 300 $\mu$m, of octadecyl and cyano phase on silica 5 $\mu$m, deposited by soaking.

QMB sensor 2: sensitive layer of thickness 150 $\mu$m, of polystyrene sulphonate phase based on a resin, deposited by soaking.

QMB sensor 3: sensitive layer of thickness 200 $\mu$m, of phenyl phase linked to a polymer in the form of a gel, deposited by soaking.

QMB sensor 4: sensitive layer of thickness 250 $\mu$m, of diamine phase on silica phase 5 $\mu$m, deposited by soaking.

QMB sensor 5: sensitive layer of thickness 100 $\mu$m, of octadecyl phase on silica 5 $\mu$m, deposited by soaking.

ISFET sensor 1: of $PbI_2$-$Ag_2S$-$As_2S_3$, membrane prepared according to the photolithographic technique.

ISFET sensor 2: of $AgCl$-$Ag_2S$, membrane prepared according to the photolithographic technique.

ISFET sensor 3: of $Sb_{metal}$, membrane prepared according to the photolithographic technique.

The measuring electrode was soaked in each sample of water for a period of 90 seconds. The output signals from each sensor were captured as from the insertion of the electrodes in each sample of water and they were measured every second over a period of 120 seconds. The maximum values of the output signals from the sensors during the capture interval were determined and were then made the subject of an analysis of main components as in the other Examples. The results of this analysis are indicated in FIG. 6A.

As for the preceding Example, the QMB sensors can be replaced by surface acoustic wave device sensors.

As a Comparative Example, this experiment was repeated in using a measuring electrode bearing only the QMB sensors 1 to 5 mentioned above. The results of this experiment are illustrated in FIG. 6B. From the graph of FIG. 6A, it is seen clearly that the system according to the invention has been able to differentiate the different samples of water as a function of the nature of the pollution concerned. Moreover, by comparing FIGS. 6A and 6B, it is clear that the use of sensors of different types of technology has enabled the apparatus according to the invention to improve the differentiation between the samples which are not capable of differentiation when the measuring electrode bears sensors of one sole type of technology.

Even if the Examples given above relate to operations of quality control of particular liquid matrices, it is necessary to understand that the present invention may be applied to the quality control of other liquid matrices and it can be applied in a lot of other fields. For example:

in foods, a few of the different applications are:
  the detection of bacteria
  the quality control of alcoholic beverages (beers, cognac, whisky, etc.) and non-alcoholic beverages (such as fruit juices, tea, coffee, etc.)
  the quality control of food oils and melted animal fats (butters, margarines, rancidity problem)
  the control of andostenone content in pig blood, which enables the removal of meat with <<boar taint>>
in the field of cosmetics:
  quality control of perfumes and other lotions
  quality control of starting materials (essential oils, etc.)
in the environmental field, the applications are also extremely wide:
  survey of drinking water distribution circuits and of used water treatments
  survey of aquatic media such as rivers and marine media
  survey of factory wastes
  detection of pesticides.
in the field of chemistry:
  quality control of solvents
  discrimination of the origins of fuels and quantification of the sulphur content levels.
in the field of medicine:
  diagnosis of vaginitis of bacterial origin by urine analysis
  diagnosis of ionic imbalance in the blood, notably in the case of poor renal function or after strong dehydration.

Although the preferred embodiments of the present invention have been given above, it is appropriate to recall that the present invention is not limited to these embodiments, which are described as non-limiting Examples.

What is claimed is:

1. An apparatus for characterising liquids, characterised in that it comprises;
   at least one measuring electrode, equipped with at least two types of sensor the respective physical or chemical reactions of which when soaked in a liquid are of different nature, the sensors of the measuring electrode (s) being non-specific sensors intended to generate respective output signals once soaked in a liquid;
   a unit for capturing the output signals emanating from the sensors; and
   a unit for processing the signals captured by the capturing unit intended for generating data which characterise a sample of liquid from the whole of the signals captured by the capturing unit when the sensors of the measuring electrode(s) are soaked in this sample of liquid.

2. The apparatus for characterising liquids according to claim 1, characterised in that the measuring electrode(s) are equipped with sensors of at least two different types selected from the group consisting of: lipid sensors, quartz microbalances, surface acoustic wave device sensors, ion-selective electrodes, chemical microelectrodes and biosensors.

3. The apparatus for characterising liquids according to claim 1, characterised in that the measuring electrode(s) are additionally equipped with at least one further sensor of one of said types present on the measuring electrode(s) but comprising a respective sensitive layer deposited according to a different procedure.

4. The apparatus for characterising liquids according to claim 1, characterised in that it further comprises at least one of the sensors selected from the group consisting of fibre optic-based sensors, pH sensors, colour sensors and temperature sensors.

5. The apparatus for characterising liquids according to claim 1, characterised in that the signal processing unit is adapted to normalise the output signals emanating from the sensors when these sensors are soaked in the sample of liquid, with respect to the difference between the respective values of the output signals originating from said sensors when these sensors are soaked in a reference liquid during a standardization phase and during the measuring phase.

6. The apparatus for characterising liquids according to claim 5, characterised in that the reference liquid corresponds to a main gustative quality such as bitter, sweet, salty, or sour.

7. The apparatus for characterising liquids according to claim 1, characterised in that it further comprises means of storing data which characterise the samples of liquids, and that the signal processing unit is intended for comparing the characterisation data, generated from a sample of liquid undergoing analysis, with stored data concerning other samples, in order to evaluate whether the sample of liquid undergoing analysis is of the same nature as a sample of liquid or of a group of samples of liquid for which data are already stored.

8. The apparatus for characterising liquids according to claim 1, characterised in that the processing unit comprises at least one module selected from the group comprising a statistical analysis module and a neural network analysis module, this or these module(s) being adapted for classifying a sample undergoing analysis with respect to data which are stored concerning other samples of liquids.

9. The apparatus for characterising liquids according to claim 1, characterised in that:

the measuring electrode(s) are equipped with sensors of at least two different types selected from the group consisting of: lipid sensors, quartz microbalances, surface acoustic wave device sensors, ion-selective electrodes, chemical microelectrodes and biosensors;

the measuring electrode(s) are additionally equipped with at least one further sensor of one of said types present on the measuring electrode(s) but comprising a respective sensitive layer deposited according to a different procedure and at least one sensor selected from the group consisting of fibre optic-based sensors, pH sensors, colour sensors and temperature sensors; and the signal processing unit is adapted to normalize the output signals emanating from the sensors when these sensors are soaked in the sample of liquid, with respect to the difference between the respective values of the output signals originating from said sensors when these sensors are soaked in a reference liquid during a standardization phase and during the measuring phase; the reference liquid corresponds to a main gustative quality such as bitter, sweet, salty or sour, it further comprises means of storing data which characterise the sample of liquid, and that the signal processing unit is intended for comparing the characterisation data, generated from a sample of liquid undergoing analysis, with stored data concerning other samples, in order to evaluate whether the sample of liquid undergoing analysis is of the same nature as a sample of liquid or of a group of samples of liquid for which data are already stored and the processing unit comprises at least one module selected from the group comprising a statistical analysis module and a neural network analysis module, this or these module(s) being adapted for classifying a sample undergoing analysis with respect to data which are stored concerning other samples of liquids.

10. A method of characterising liquids, this method being characterised in that it comprises at least the following steps:

equipping at least one measuring electrode with two types of sensor the respective physical or chemical reactions of which when soaked in a liquid are of different nature, the sensors of the measuring electrode(s) being non-specific sensors;

soaking the measuring electrode(s) in a sample of the liquid to be characterised;

capturing the output signals originating from said sensors when these sensors are soaked in the liquid; and processing the signals captured so that the data which characterise the sample of liquid are generated from the whole of the signals captured.

11. The method of characterising liquids according to claim 10, characterised in that it comprises the step of equipping the measuring electrode(s) with sensors of at least two different types selected from the group consisting of: lipid sensors, quartz microbalances, surface acoustic wave device sensors, ion-selective electrodes, chemical microelectrodes and biosensors.

12. The method of characterising liquids according to claim 10, this method being characterised in that it comprises the step of measuring the properties of the sample of liquid in employing at least one of the sensors selected from the group consisting of fibre optic-based sensors, pH sensors, colour sensors and temperature sensors, the signals which represent the properties thus measured being captured and processed together with the output signals originating from the sensors of the measuring electrode(s).

13. The method of characterising liquids according to claim 10, this method being characterised in that it comprises a prior step of standardization during which the measuring electrode(s) are soaked in at least one reference sample, a step of capturing the output signals originating from said sensors when these sensors are soaked in each reference sample, and an additional step of capturing output signals originating from the sensors when these sensors are soaked once more in the at least one reference sample(s), and in that the signal processing step comprises an operation of normalization with respect to the difference between the values of the output signals captured during the standardization step and during the additional signal capture step.

14. The method of characterising liquids according to claim 13, characterised in that the at least one reference liquid corresponds to a main gustative quality such as bitter, sweet, salty or sour.

15. The method of characterising liquids according to claim 10, this method being characterised in that it further comprises a step of storing, in a storage means, data which characterise the samples of liquids, and in that said step of processing the signals comprises an operation of comparing the characterisation data, generated from a sample of liquid undergoing analysis, with stored data concerning other samples, in order to evaluate whether the sample of liquid undergoing analysis is of the same nature as a sample of liquid or of a group of samples of liquid for which data are already stored.

16. The method of characterising liquids according to claim 10, this method being characterised in that the signal processing step comprises at least one operation selected from the group consisting of a statistical analysis operation and a neural network analysis operation; the operation(s) being adapted for classifying a sample undergoing analysis with respect to classes established in a prior learning phase.

17. The method of characterising liquids according to claim 10, this method being characterised in that it further comprises a step of cleaning the measuring electrode(s) consisting of soaking said electrode(s) in an additional sample of fluid.

18. The method of characterising liquids according to claim 10, characterised in that;

it comprises the step of equipping the measuring electrode(s) with sensors of at least different two types selected from the group consisting of: lipid sensors, quartz microbalances, surface acoustic wave device sensors, ion-selective electrodes, chemical microelectrodes and biosensors;

it comprises the step of measuring the properties of the sample of liquid in employing at least one of the sensors selected from the group consisting of fibre optic-based sensors, pH sensors, colour sensors and temperature sensors, the signals which represent the properties thus measured being captured and processed together with the output signals originating from the sensors of the measuring electrode(s);

it comprises a prior step of standardization during which the measuring electrode(s) are soaked in at least one reference sample, a step of capturing the output signals originating from said sensors when these sensors are soaked in each reference sample, and an additional step of capturing output signals originating from the sensors when these sensors are soaked once more in the at least one reference sample(s), and in that the signal processing step comprises an operation of normalization with respect to the difference between the values of the output signals captured during this standardization step and during the additional signal capture step;

the at lest one reference sample corresponds to a main gustative quality such as bitter, sweet, salty, or sour, it further comprises a step of storing, in a storage means, data which characterise the samples of liquids, and in that the step of processing the signals comprises an operation of comparing the characterisation data, generated from a sample of liquid undergoing analysis, with stored data concerning other samples, in order to evaluate whether the sample of liquid undergoing analysis is of the same nature as a sample of liquid or of a group of samples of liquid for which data are already stored;

the signal processing step comprises at least one operation selected from the group consisting of a statistical analysis operation and a neural network analysis operation; the operation(s) being adapted for classifying a sample undergoing analysis with respect to classes established in a prior learning phase; and it further comprises a step of cleaning the measuring electrode(s) consisting of soaking said electrodes in an additional sample of fluid.

* * * * *

UNITED STATES PATENT AND TRADEMARK OFFICE
CERTIFICATE OF CORRECTION

PATENT NO.   : 6,290,838 B1
DATED        : September 18, 2001
INVENTOR(S)  : Jean-Christophe Mifsud et al.

Page 1 of 1

It is certified that error appears in the above-identified patent and that said Letters Patent is hereby corrected as shown below:

<u>Column 1,</u>
Line 48, "liquid" should read -- lipid --; and

<u>Column 8,</u>
Line 22, "carries" should read -- carried --.

Signed and Sealed this

Fourteenth Day of January, 2003

JAMES E. ROGAN
*Director of the United States Patent and Trademark Office*